(12) United States Patent
Goble et al.

(10) Patent No.: US 10,770,175 B2
(45) Date of Patent: Sep. 8, 2020

(54) SYSTEM AND METHOD FOR SEGMENTATION AND VISUALIZATION OF MEDICAL IMAGE DATA

(71) Applicant: MULTUS MEDICAL, LLC, Tempe, AZ (US)

(72) Inventors: Warren Goble, Tucson, AZ (US); Sandeep Shah, Tempe, AZ (US)

(73) Assignee: MULTUS MEDICAL LLC, Tempe, AZ (US)

( * ) Notice: Subject to any disclaimer, the term of this patent is extended or adjusted under 35 U.S.C. 154(b) by 85 days.

(21) Appl. No.: 16/131,503

(22) Filed: Sep. 14, 2018

(65) Prior Publication Data

US 2019/0088360 A1    Mar. 21, 2019

Related U.S. Application Data

(60) Provisional application No. 62/559,052, filed on Sep. 15, 2017.

(51) Int. Cl.
| | |
|---|---|
| *G06T 11/00* | (2006.01) |
| *G16H 30/40* | (2018.01) |
| *G16H 30/20* | (2018.01) |
| *G06T 7/00* | (2017.01) |
| *G06T 19/20* | (2011.01) |
| *G16H 50/50* | (2018.01) |
| *G06T 13/20* | (2011.01) |

(52) U.S. Cl.
CPC .......... *G16H 30/40* (2018.01); *G06T 7/0014* (2013.01); *G06T 19/20* (2013.01); *G16H 30/20* (2018.01); *G16H 50/50* (2018.01); *G06T 13/20* (2013.01); *G06T 2207/10072* (2013.01); *G06T 2207/20084* (2013.01); *G06T 2207/30012* (2013.01); *G06T 2210/41* (2013.01); *G06T 2219/004* (2013.01); *G06T 2219/2004* (2013.01); *G06T 2219/2012* (2013.01)

(58) Field of Classification Search
CPC .. G06K 9/64; G06K 9/60; G06K 9/48; G06K 9/4604; G06K 9/00536; G06K 9/00637; G06K 9/4652; G06F 17/30044; G06F 17/30244; G06T 7/0012; G06T 5/00; G06T 7/50
USPC .......................... 382/128, 103, 149, 145, 201
See application file for complete search history.

(56) References Cited

U.S. PATENT DOCUMENTS

| | | | |
|---|---|---|---|
| 4,341,120 A | 7/1982 | Anderson | |
| 4,630,203 A | 12/1986 | Szirtes | |
| 6,028,907 A | 2/2000 | Adler et al. | |
| 6,234,968 B1 | 5/2001 | Sumanaweera et al. | |

(Continued)

*Primary Examiner* — Phuoc H Doan
(74) *Attorney, Agent, or Firm* — Weiss & Moy, P.C.; Jeffrey D. Moy

(57) ABSTRACT

A computing device has a processor. A display is coupled to the processor. A user interface is coupled to the processor for entering data into the computing device. A memory is coupled to the processor, the memory storing program instructions that when executed by the processor, causes the processor to: load medical image data; match the medical image data to an anatomical model stored in a database having a data set closest to the medical image data; adjust at least one property on the anatomical model to form a modified anatomical model to match the medical data image; and detect if areas on the modified anatomical model exceeds predefined ranges indicating potential injured areas.

20 Claims, 14 Drawing Sheets

(56) References Cited

U.S. PATENT DOCUMENTS

| | | | |
|---|---|---|---|
| 6,482,160 | B1 | 11/2002 | Stergiopoulos et al. |
| 7,824,338 | B2 | 11/2010 | Daft et al. |
| 7,903,856 | B2 | 3/2011 | Pfister et al. |
| 9,330,490 | B2 | 5/2016 | Weersink et al. |
| 9,451,927 | B2 | 9/2016 | Cetingul et al. |
| 9,478,009 | B2 | 10/2016 | Stazzone |
| 2013/0195341 | A1 | 8/2013 | Liu et al. |
| 2016/0051843 | A1 | 2/2016 | Sumanaweera et al. |
| 2019/0340837 | A1* | 11/2019 | Shmayahu ............ A61B 90/37 |

* cited by examiner

FIG. 5A
FIG. 5B
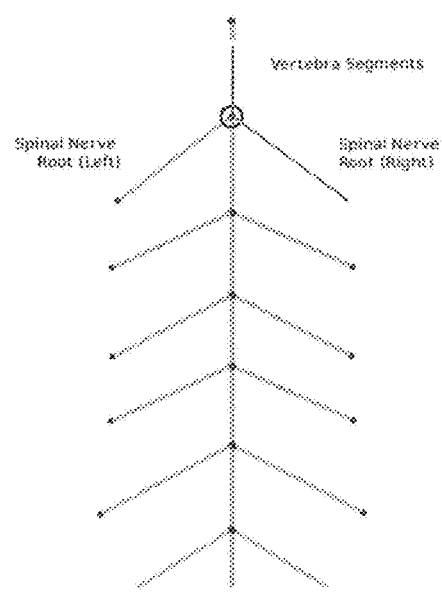
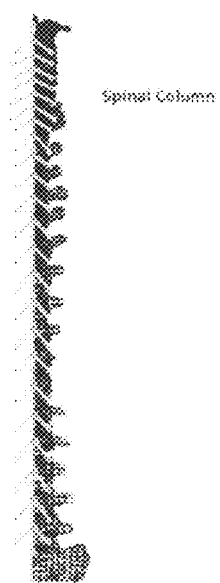

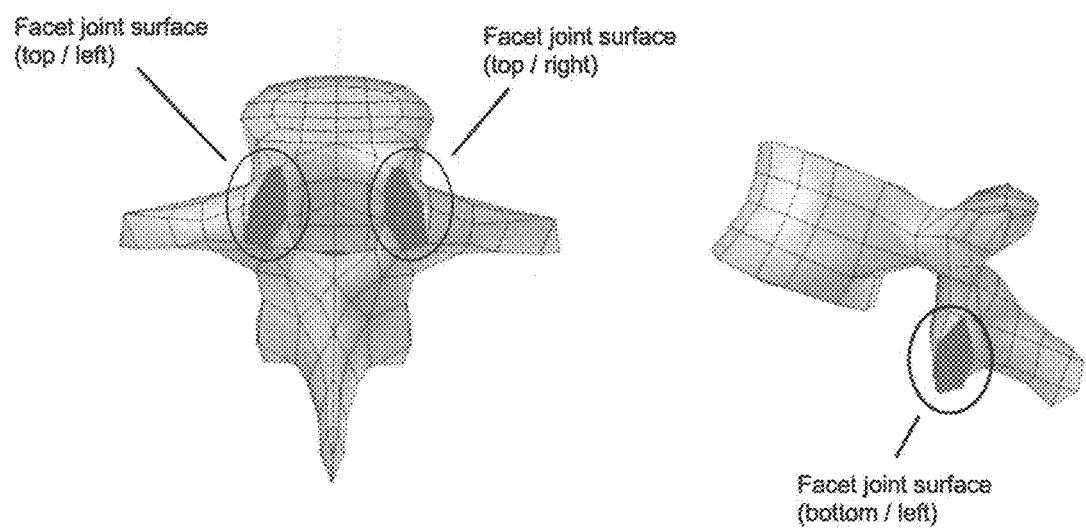

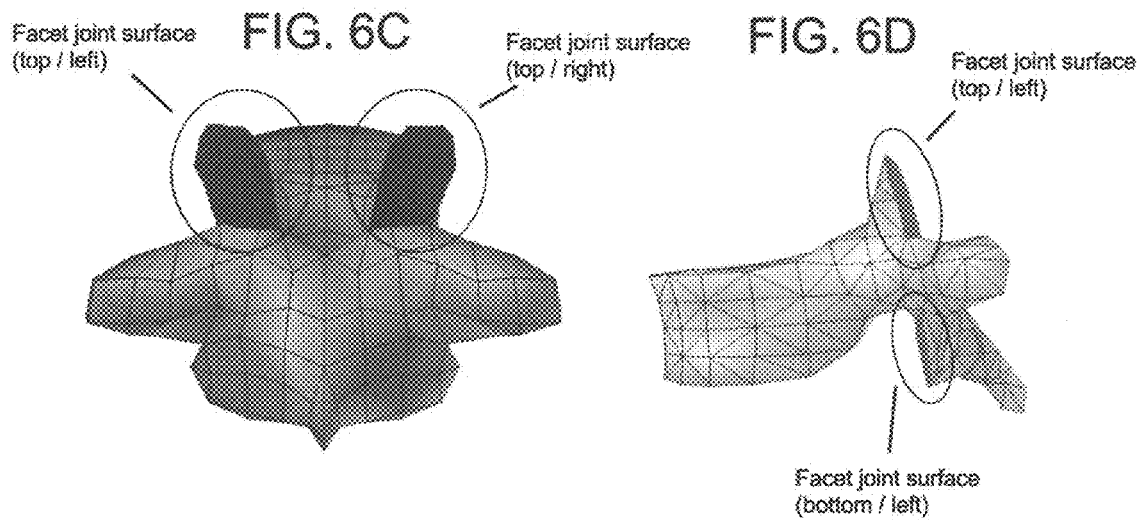

SYSTEM AND METHOD FOR SEGMENTATION AND VISUALIZATION OF MEDICAL IMAGE DATA

This patent application is related to U.S. Provisional Application No. 62/559,052 filed Sep. 15, 2017, entitled "SYSTEM AND METHOD FOR SEGMENTATION AND VISUALIZATION OF MEDICA IMAGE DATA" in the name of the same inventors, and which is incorporated herein by reference in its entirety. The present patent application claims the benefit under 35 U.S.C § 119(e).

FIELD

The present application generally relates to a medical image data, and, more particularly, to a system and method for the segmentation and visualization of medical image data such as Magnetic Resonance Imaging data (MRI).

BACKGROUND

Medical imaging is the technique and process of creating visual representations of the interior of a body for clinical analysis and medical intervention, as well as visual representation of the function of some organs or tissues. Medical imaging seeks to reveal internal structures hidden by the skin and bones, as well as to aid in the diagnosis and treatment of diseases.

The advent of data-driven medicine and modern computing power has enabled patient-specific diagnosis and treatment based on medical imaging data. However, the primary bottle-neck in this workflow remains the ability to efficiently segment medical imaging data for use in simulation, modeling, visualization, animation and statistical analysis. Segmentation and visualization of medical image data such as MRI is a complex task. Manual image segmentation for a single CT or MRI scan is a complex process, often requiring expensive, specialized software and many hours of work to segment a single image sequence. As an image processing problem, medical image segmentation also poses many significant challenges due to noisy data, low contrast images, and large variations between patients. However, ultimately most segmentation implementations are trying to solve a single problem, which is classifying pixels of a medical image into some sort of anatomical structure or other anatomical abnormalities such as an injury or disease.

Using simple segmentation tasks such as using the threshold value of an image works fairly well with CT images. This is because CT images represent density of material similar to an X-ray image. Using threshold values may work for segmenting high density materials such as bones, but lacks the resolution to tell the differences between soft tissues. MRI imaging shows differences of soft tissues very well, but requires a more complex data driven approach to solving the classification problem.

SUMMARY

In accordance with one embodiment, a computing device is disclosed. The computing device has a processor. A display is coupled to the processor. A user interface is coupled to the processor for entering data into the computing device. A memory is coupled to the processor, the memory storing program instructions that when executed by the processor, causes the processor to: load medical image data; match the medical image data to an anatomical model stored in a database having a data set closest to the medical image data; adjust at least one property on the anatomical model to form a modified anatomical model to match the medical data image; and detecting if areas on the modified anatomical model exceeds predefined ranges indicating potential injured areas.

In accordance with one embodiment, a computing device is disclosed. The computing device has a processor. A display is coupled to the processor. A user interface is coupled to the processor for entering data into the computing device. A memory is coupled to the processor, the memory storing program instructions that when executed by the processor, causes the processor to: load medical image data; match the medical image data to an anatomical model stored in a database having a data set closest to the medical image data, the anatomical model being a three-dimensional anatomical model; adjust at least one property on the three-dimensional anatomical model to form a modified three-dimensional anatomical model to match the medical data image; detect if areas on the modified three-dimensional anatomical model exceeds predefined ranges indicating potential injured areas; store the modified three-dimensional anatomical model in the database as a new three-dimensional anatomical model; and form one of an automated video or animation creation of the modified three-dimensional anatomical model.

BRIEF DESCRIPTION OF THE DRAWINGS

Embodiments of the disclosure will become more fully understood from the detailed description and the accompanying drawings, wherein:

FIGS. 5A-5D are illustrations of a 3D model of a spine according to one embodiment of the present invention;

FIGS. 6A-6E are illustrations of a 3D model of showing facet joints of the vertebra according to one embodiment of the present invention;

DESCRIPTION OF THE INVENTION

The description set forth below in connection with the appended drawings is intended as a description of presently preferred embodiments of the disclosure and is not intended to represent the only forms in which the present disclosure can be constructed and/or utilized. The description sets forth the functions and the sequence of steps for constructing and operating the disclosure in connection with the illustrated embodiments. It is to be understood, however, that the same or equivalent functions and sequences can be accomplished by different embodiments that are also intended to be encompassed within the spirit and scope of this disclosure as well as for other anatomical structures of the body, for example shoulder and knees.

The present system and method may allow one to upload medical image data. The medical image data may be analyzed and aligned with a three dimensional (3D) model of the area of the body associated with the medical image data. Using the present system, one may manually adjustments to the 3D model. One may add specific injuries and/or body abnormalities to the 3D model. Thus, one may be able to adjust the 3D model to match the features found in the medical imaging data. One may then save the 3D model that now contains the medical image data. Ultimately, the application is designed to automatically save if there is a change done manually through the user interface. One may also use the methods to create an animation to outline a surgical procedure.

Figure 1:
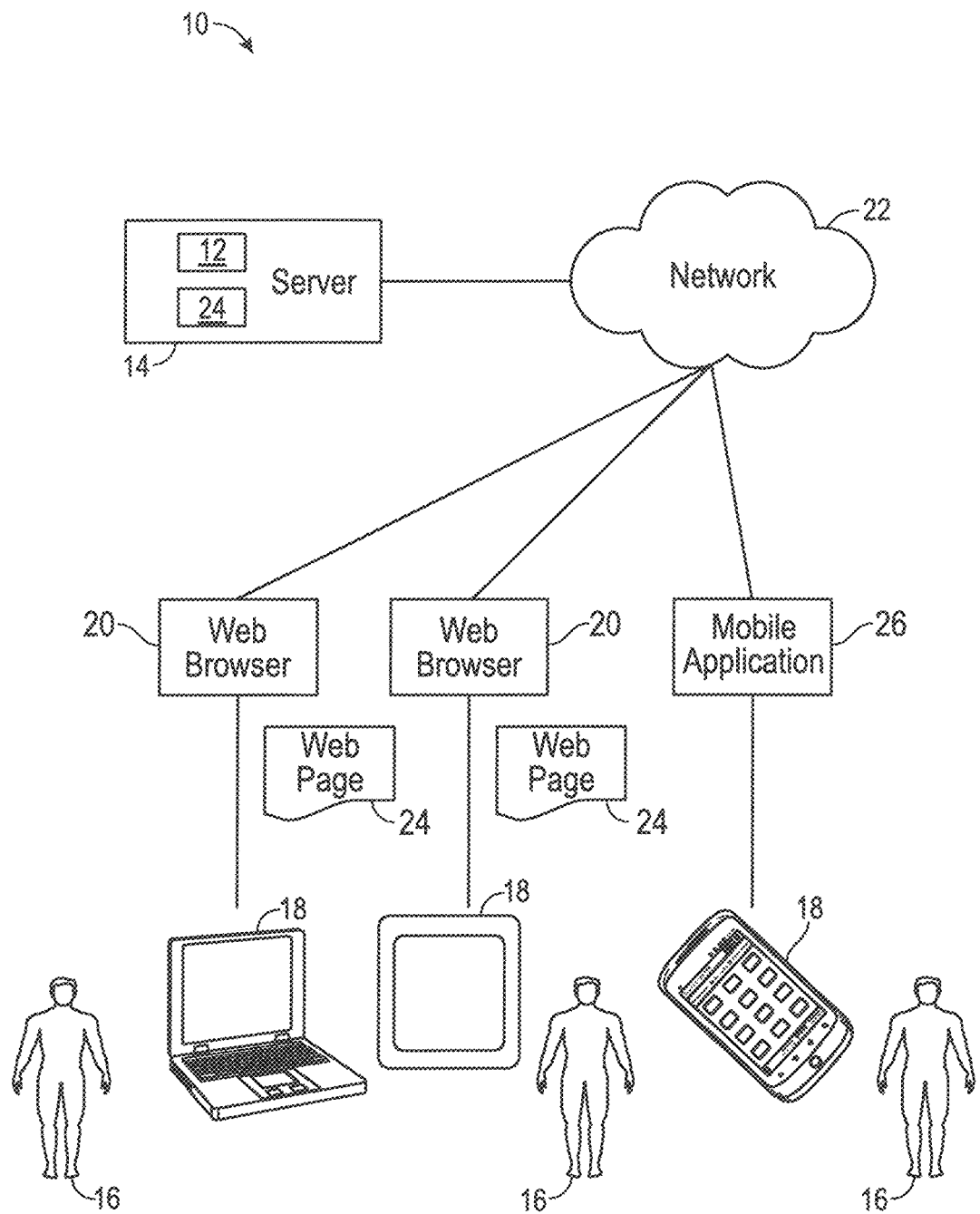
FIG. 1 is a block diagram of a system for forming 3D images from medical data images according to one embodiment of the present invention.

Referring now to FIG. 1, a system 10 may be shown. The system 10 may read medical image data such as MRIs, CT and the like. The system 10 may match anatomical structures to the image data received and produce 3D models, 2D/3D/ videos, 2D/3D images and animations showing pathological injuries. The system 10 may have a server 14. The server 14 may be used to host an application 12 of the present invention. Individuals 16 may use one or more computing devices 18 to access the application 12 that may be hosted on the server 14. The computing devices 18 may be a personal computer system, tablet device, handheld or laptop device, mobile phone device, server computer system, multiprocessor system, microprocessor-based system, set top boxes, programmable consumer electronics, network PCs, and distributed cloud computing environments that include any of the above systems or devices, and the like. The computing device 18 may be described in the general context of computer system executable instructions, such as program modules, being executed by a computer system as may be described below.

The computing device 18 may be loaded with an operating system. The operating system of the computing device 18 may manage hardware and software resources of the computing device 18 and provide common services for computer programs running on the computing device 18. The computing device 18 may be loaded with a web browser 20. The web browser 20 may allow the computing device 18 to gain online access to a network 22 such as the World Wide Web. The web browser 20 may be Microsoft® Internet Explorer, Google® Chrome, Mozilla® Firefox, Apple® Safari or similar browsing applications. By connecting to the network 22, the computing device 18 may access a website 24 associated with the application 12 hosted on the server 14.

Alternatively, or in addition to, the computing device 18 may download the application 12 to the computing device 18. In this manner, the computing device 18 may run the application 12 directly. If the computing device 18 is a mobile computing device, the application 12 may be a mobile application 26. The mobile application 26 may access and communicate with the application 12 hosted on the server 14. By connecting to the network 22, the computing device 18 may access and communicate with the application 12 hosted on the server 14 via the mobile application 26.

Figure 2:
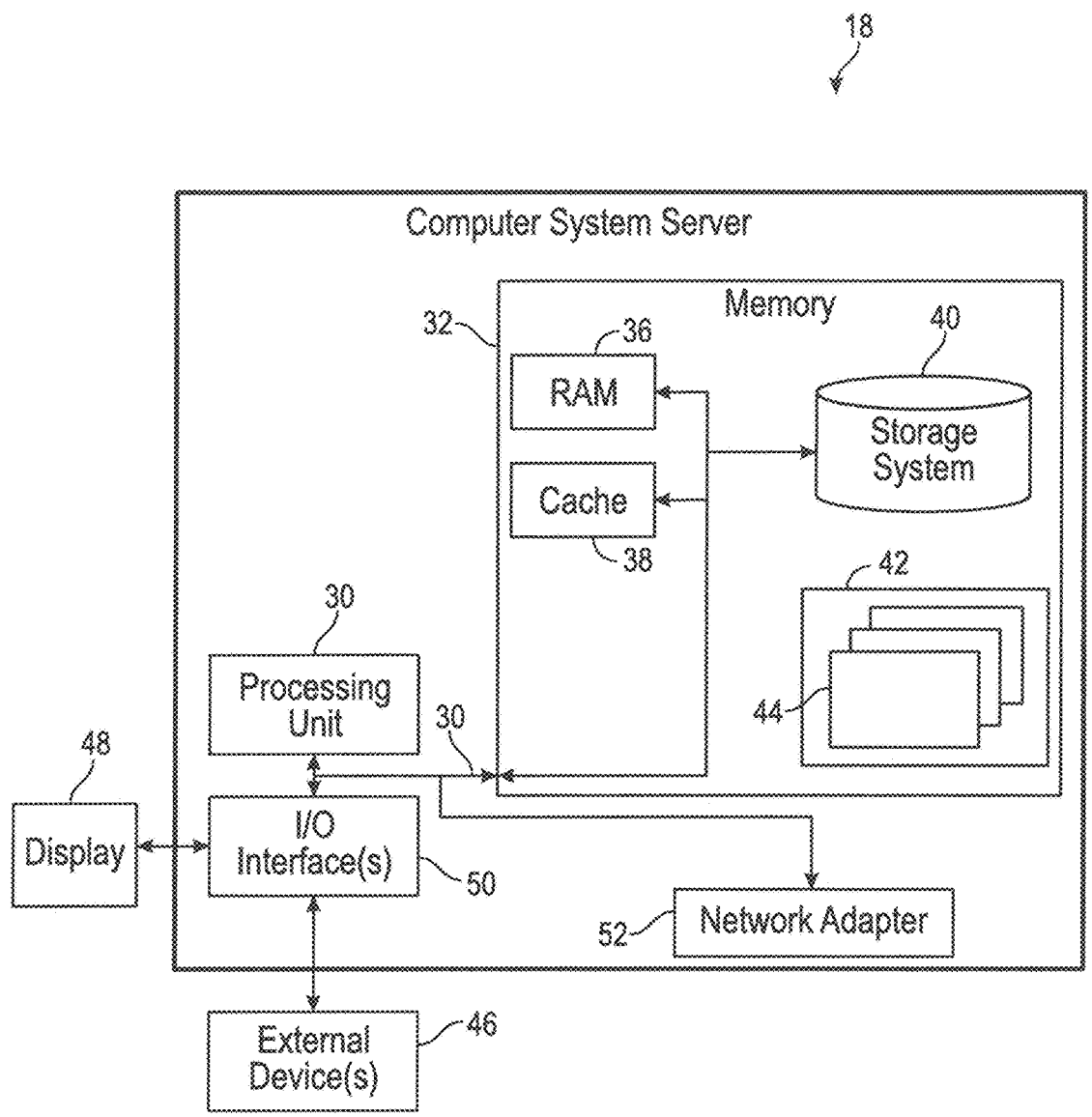
FIG. 2 is a block diagram showing a computer system/server used in the system of FIG. 1 according to one embodiment of the present invention.

Referring now to FIG. 2, the computing devices 18 and/or the server 14 hosting the application 12 may be described in more detail in terms of the machine elements that provide functionality to the systems and methods disclosed herein. The components of the computing devices 18 and/or server 14 may include, but are not limited to, one or more processors or processing units 30, a system memory 32, and a system bus 34 that couples various system components including the system memory 32 to the processor 30. The computing devices 18 and/or server 14 may typically include a variety of computer system readable media. Such media could be chosen from any available media that is accessible by the computing devices 18 and/or server 14, including non-transitory, volatile and non-volatile media, removable and non-removable media. The system memory 32 could include one or more computer system readable media in the form of volatile memory, such as a random access memory (RAM) 36 and/or a cache memory 38. By way of example only, a storage system 40 may be provided for reading from and writing to a non-removable, non-volatile magnetic media device typically called a "hard drive" or Solid State Drive (SSD). The computing device 18 may also use a storage system such as a cloud infrastructure. Cloud based storage may use services such as Azure, Amazon Web Services or other cloud based storage systems.

The system memory 32 may include at least one program product/utility 42 having a set (e.g., at least one) of program modules 44 that may be configured to carry out the functions of embodiments of the invention. The program modules 44 may include, but is not limited to, an operating system, one or more application programs, other program modules, and program data. Each of the operating systems, one or more application programs, other program modules, and program data or some combination thereof, may include an implementation of a networking environment. The program modules 44 generally carry out the functions and/or methodologies of embodiments of the invention as described herein. For example, the program modules 44 may contain the application 12 carry out the steps for monitor and identify employees who may begin to actively seek new employment and other functionality as will be described below.

The computing device 18 and/or server 14 may communicate with one or more external devices 46 such as a keyboard, a pointing device, a display 48, and/or any similar devices (e.g., network card, modem, Bluetooth etc.). Such communication may occur via Input/Output (I/O) interfaces 50 or wirelessly. Alternatively, the computing devices 18 may communicate with one or more networks such as a local area network (LAN), a general wide area network (WAN), and/or a public network (e.g., the network 24 shown in FIG. 1) via a network adapter 52. As depicted, the network adapter 52 may communicate with the other components of the computing device 18 via the bus 36.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, aspects of the disclosed invention may take the form of a computer program product embodied in one or more computer readable media having computer readable program code embodied thereon.

Any combination of one or more computer readable media (for example, storage system 40) may be utilized. In the context of this disclosure, a computer readable storage medium may be any tangible or non-transitory medium that can contain, or store a program (for example, the program product 42) for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing.

The present system and method differs from the prior art systems and methods which try to generate geometry of the area directly from the medical image data. In contrast, the present system and method uses existing models and datasets to create a modified dataset as well be described below.

In general, the present system and method may use a more advanced data driven approach to classifying medical image data, which may implements multiple data driven approaches:

1. Pre-defining anatomical constraints & surfaces—Assigning these constraints allows future automation assistance to be integrated into the application at a later date. For example, discs will be anatomically connected between two vertebras. The connection surfaces are predefined based on normalized anatomical location. Another example is the spinal cord will always be constrained through a hole near the center of the vertebra called vertebral foramen.

2. Anatomical structure reduction. The anatomical structures/objects are broken down into properties and shape components (See FIG. 4B). Anatomical structures will be somewhat normalized across all humans, but just like a fingerprint not everyone's genetic code is identical. Differences between humans may be adjusted as simple properties and measurements defined for a specific anatomical structure. This may allow information to be broken down into simple properties assigned to a dataset that may be adjusted to cover a wide range of human anatomy. Some anatomical structures contain anatomical processes. These processes are additional data structures that serve as properties that can be adjusted also and are common across all humans. In anatomy, a process may be defined as a projection or outgrowth of tissue from a larger body. For example, in a vertebra, a process may serve for muscle attachment and leverage (as in the case of the transverse and spinous processes), or to fit (forming a synovial joint), with another vertebra (as in the case of the articular processes). A solution proposed in the present invention uses shape components and properties to create 3D geometry of objects using a procedure where software code can be composed to create geometry dynamically. Additionally, geometry meshes can be used in combination with shape components. This method is referred to a skinning of a mesh using bones.

Figure 7A:
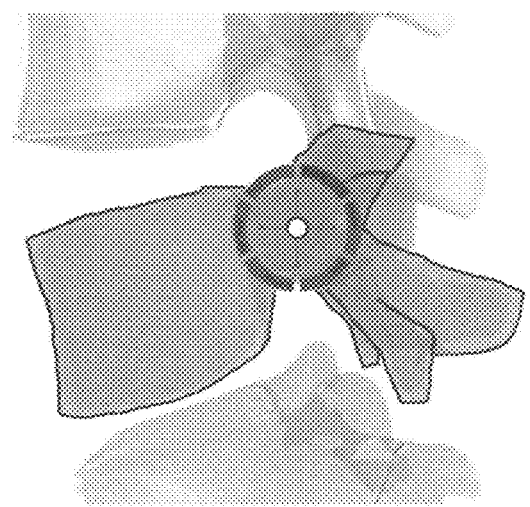
FIGS. 7A-C are illustrations showing 3D user interface tools and a menu for manual property adjustments.
Figure 7B:
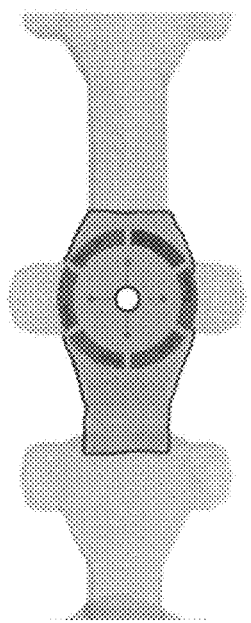
Figure 7C:
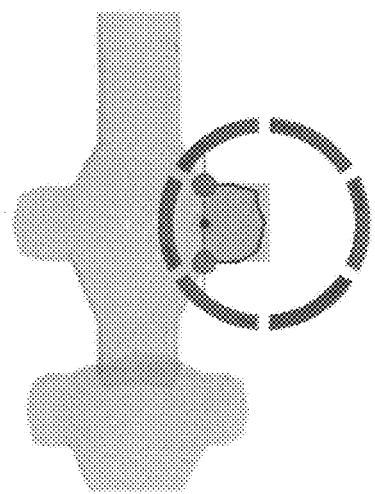

3. 3D user interface and tools—Human interaction through a user interface consisting of property adjusters for manually manipulation of properties in the dataset contained in a 3D viewport (See FIGS. 7A-C). The system and method may have tools to speed the manual manipulation of properties, which for example can be constrained to volumetric area, axis and/or programmatic constraint relative to any other object and/or dataset property. User interface meaning any display device and input device such as a screen, touchscreen, monitor, VR headset, mouse, keyboard, game controller, wireless camera tracking, VR head tracking and similar I/O devices. Additionally, anatomical objects may have sub structures such as processes or roots. For example, the spinal cord will have nerve root that can be selected separately and properties can then be adjusted for that sub object or section (See FIGS. 7B-7C). This method applies to any anatomical object that is defined statically or dynamically such as the disc between vertebra.

4. Automated algorithms may be used on physical normalized constraints to detect injuries. For example a database of properties can be used to create a normalized database. This can be used to detect properties that are out of range of normal properties. Additionally, constraints can be programmatically composed using software code. This allows additional algorithms to be added for connecting tissues such as ligaments, tendons and muscles 5. Machine learning algorithms may be used to automate the manipulation of dataset properties. One of the main approaches to using a data solution is the ability to train existing datasets using the properties stored for previous datasets. Over time this will improve accuracy for automated processes. Moreover, training or deep learning using reduced datasets or properties allows significant performance improvements overusing image based learning. In theory training a machine using a hybrid of properties and images adds additional accuracy and more statistical options. For example a hybrid machine learning and/or hybrid deep learning algorithm can use Convolution based image Neural Network (CNN) and based on the properties define a region in 3D space to look for instead of sweeping the entire image. This makes the image based recognition more optimized and accurate. Machine based algorithm such as Support Vector Machines, Deep learning, Neural Networks, Object detection, Feature detection and such can be composed together to generate statistical results.

6. The system and method may use existing reusable datasets, which have been created manually using user interface and/or created using automated processes described above in paragraph 5. The system and method may start with making a copy of an existing nominal or selected dataset and adjust the properties of the dataset to match with the MRI or CT image features. This is different than taking the approach of trying to generate 3D models directly from MRI or CT images using image based algorithms which create voxels or 3D geometry.

Figure 9A:
FIGS. 9A-C are illustrations showing the application slice/cross section function according to one embodiment of the present invention.
Figure 9B:
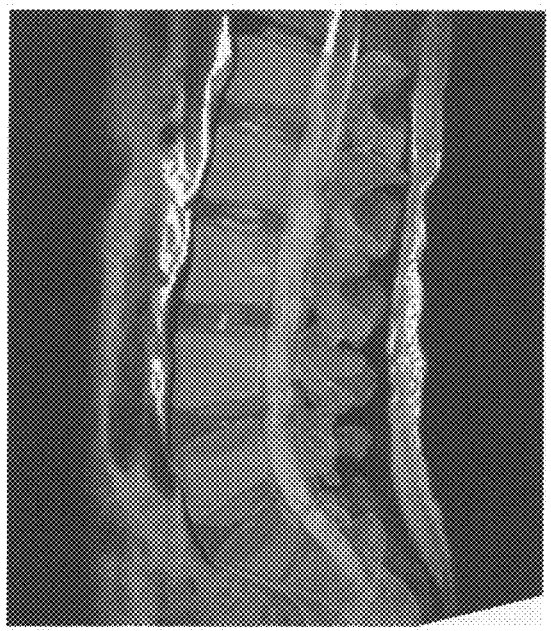
Figure 9C:
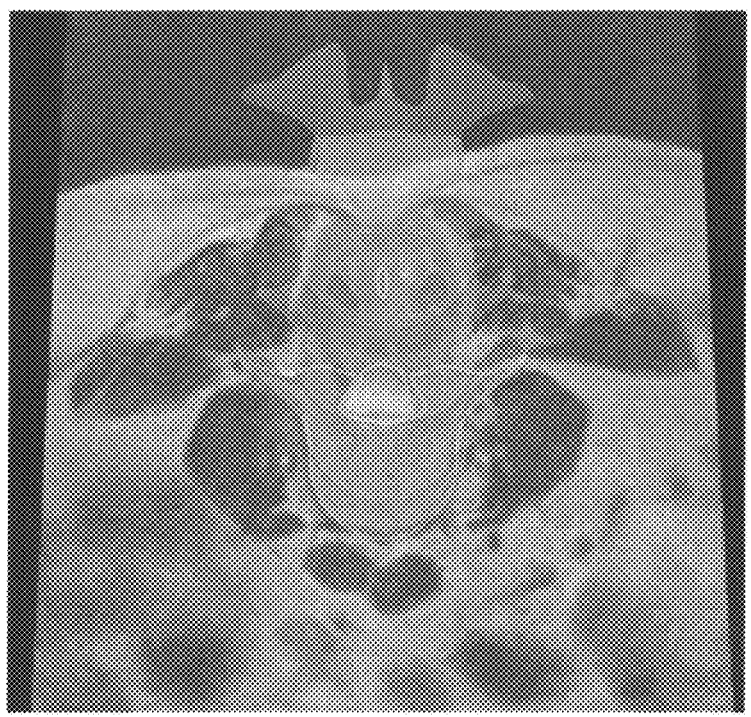

7. Automated video and animation creation. Since all injuries are composed visually the application has a list of injuries tracked in memory, software code can then automate the entire video creation and keyframe each frame automatically to create an interactive or static video o and/or animation sequence. The keyframed sequence of events can then be pushed through a component or function, which software rendering code will render an image for an individual frame. The rendered image frame sequence can then be composed into a video file using a modern codecs such as H.265 or compatible standard. Video and animation sequences can contain a variety of objects and overlaid elements such as labels, which the rendering code will include and compose into a sequence of keyframed images. Pro-defined keyframes or generic elements such as rotations, image slices, zooming, toggling objects visibility can be composed anywhere inside of the video sequence. Additionally the application has an image slicing function which slices all the intersecting geometry and displays the intersecting contours directly on the selected image. (See FIGS. 9A-C).

The present system and method using the above conditions allow for better separation between the image algorithms and dataset, which allows better maintainability and composability using a range of imaging algorithms or machine learning classifiers. Additionally, a new dataset is copied from a previous one and the new dataset created is a copy with any modified properties. The dataset is always immutable, meaning properties from an existing dataset are never modified, instead an entire copy of the dataset is made and changes to the properties are done during the creation or copy process. This method is referred to as Copy-on-write (COW). The big advantage of using this data model is you never delete anything and always have copies, which can be integrated into machine and statistical software code. In theory over time machines can learn how to segment based on human's interactions via user interface during the segmentation process.

The system and method creates a plurality of different models related to various anatomical structures of the body. Multiple models may be formed of a same or similar anatomical structure, each model having differing characteristics. When medical imaging data is loaded, the system and method may match the medical imaging data to the closet dataset by using multiple mentions such as manually assigned default datasets, and statistical methods used with a combination of Artificial Intelligence (AI) and/or Machine Learning.

Figure 3:
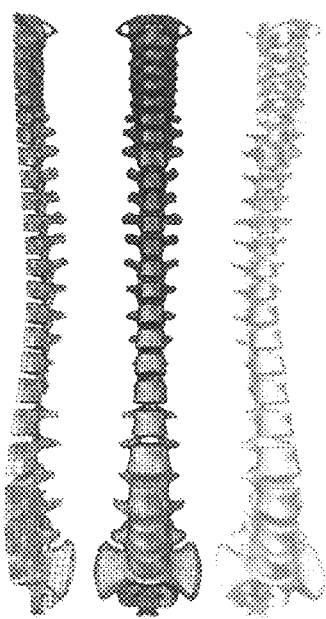
FIG. 3 is an illustration of a 3D model of a spine according to one embodiment of the present invention.

Referring to FIG. 3, model creation of a spine may be disclosed. As shown in FIG. 3, a 3D representation of a spine may be seen. The present embodiment may be seen as an example and should not be seen in a limiting manner. The 3D representation of the anatomical area may be formed in different manners. In accordance with one embodiment, polygon modeling may be used. Polygon modeling is an approach for modeling objects by representing or approximating their surfaces using polygons/faces connected by a series of vertices representing points in 3D space. Alternatively, other methods of representing 3D objects may be used such as, but not limited to: NURBS surfaces, subdivision surfaces, and equation-based representations used in ray tracers. Volumetric rendering methods can also be applied to render 3D views. In some cases, the application may use a hybrid of rendering methods to achieve the desired visual result.

Procedural object creation is a functional method of creating geometry using code. Simple geometry by itself does not define much and works well for dealing with visualizations that are mostly static. Anatomical structures in the human body contain many types of properties and constraints. Functional methods also are designed to have sub-modules applied to them, which allows additional customization using composition. Each function can be designed to use input parameters to make detailed adjustments to the object or generate geometry defined using code and higher order functions.

The system and method may be designed to allow detailed adjustments to specific shape components and/or properties of the anatomical structure. This may allow a user to adjust the model of the anatomical structure to conform to the medical data image. Thus, in the example above, the normal anatomy of the spine is usually described by dividing up the spine into three major sections: the cervical, the thoracic, and the lumbar spine. Each section is made up of individual bones, called vertebrae. There are 7 cervical vertebrae, 12 thoracic vertebrae, and 5 lumbar vertebrae.

Figure 4A:
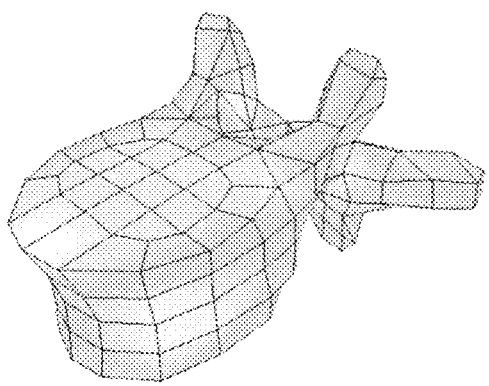
FIGS. 4A-4C are illustrations of a 3D model of a vertebra according to one embodiment of the present invention.
Figure 4B:
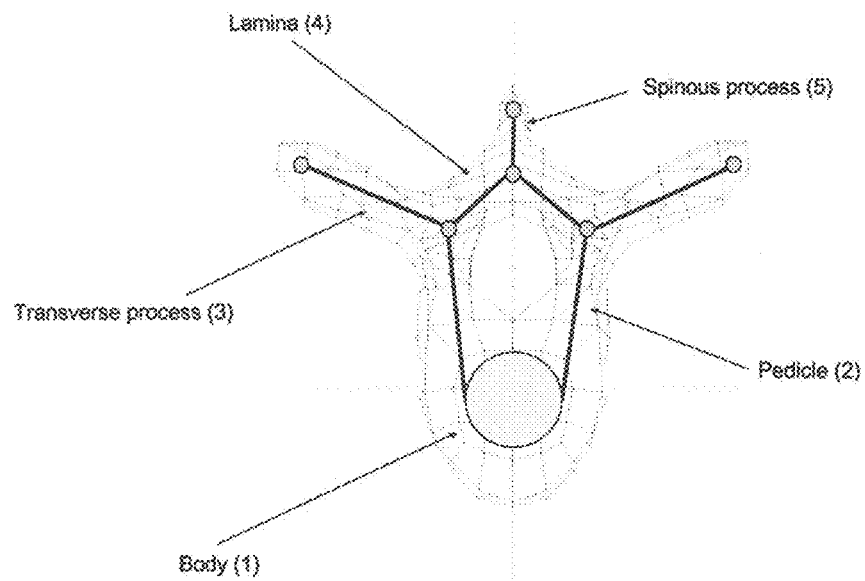
Figure 4C:
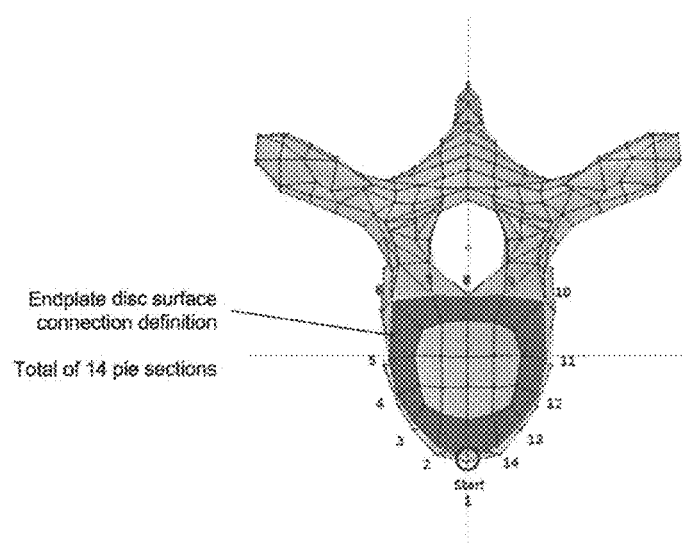

An example of a spine may be seen in FIGS. 4A-4C, where the individual vertebrae model may be made up of several different components. The following components shown in FIG. 4B will have properties that can be defined for each such as height radius, thickness, length, position, scale or a custom defined properties such as additional injuries. The body 1 of the vertebra is the primary area of weight bearing and provides a resting place for the fibrous discs which separate each of the vertebrae. Additionally, the same applies for pedicle 2, transverse process 3, lamina 4, spinous process 5, and any additional shape components and/or properties. The shape mesh and shape definition can represent any anatomical object with assigned properties.

The system and method may allow the user to adjust specific individual vertebrae. The initial vertebrae model may be formed through polygon modeling as shown in the present embodiment. A polygon mesh, which is a collection of vertices, edges and faces, may be used to define the shape of the initial vertebrae model. The polygon mesh can also be constrained to the properties of the vertebra processes of components. The vertebral disc may be mostly constraint by the end plates of the vertebrae, which has a defined shape which can be adjusted as a property (See FIG. 4C). The height of the disc may be dynamic to show compression, which in the case can be a test measurement between these points on two adjacent vertebras.

In general, each vertebra should have a consistent defined geometry. The vertebra end plate (outer perimeter of the body A) may be defined as containing 14 quads (FIG. 4C). This may also define the connection constraint. Vertex groups may be used to tag the vertices belonging to parts of the vertebra. For example, two vertex groups may define the outside and inside of the disc annulus (See FIG. 4C).

A sweeping method function may be used to create the surface geometry. Sweeping may be defined as the process of moving along an open/closed path of points in 3D space and a function will generate surface geometry using software code. This method creates the surface geometry instead of using static geometry that is pre-defined. The geometry is created dynamically using software code.

Referring to FIGS. 5A-5D, the system and method may have a spinal cord function. The spinal cord function may use an initial defined set of connected segments. The mesh may be defined as a hierarchical list of connecting segments (bones) containing no geometry such as triangles or quads. The connecting segments may be stored in a hierarchical tree, with C1 being the root node. As disclosed above, the cervical spine is comprised of seven vertebrae: C1, C2, C3, C4, C5, C6, and C7. These vertebrae begin at the base of the skull (C1) and extend down to the thoracic spine having seven vertebrae: T1, T2, T3, T4, T5, T6, and T7 down to the lumbar spine having vertebrae: L1, L2, L3, L4, L5, L6, and L7.

Figure 5C:
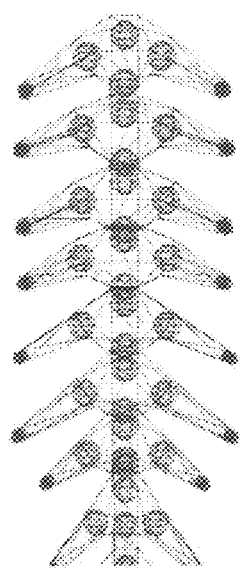
Figure 5D:
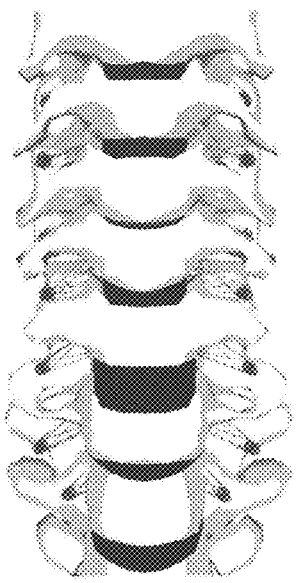
Figure 6E:
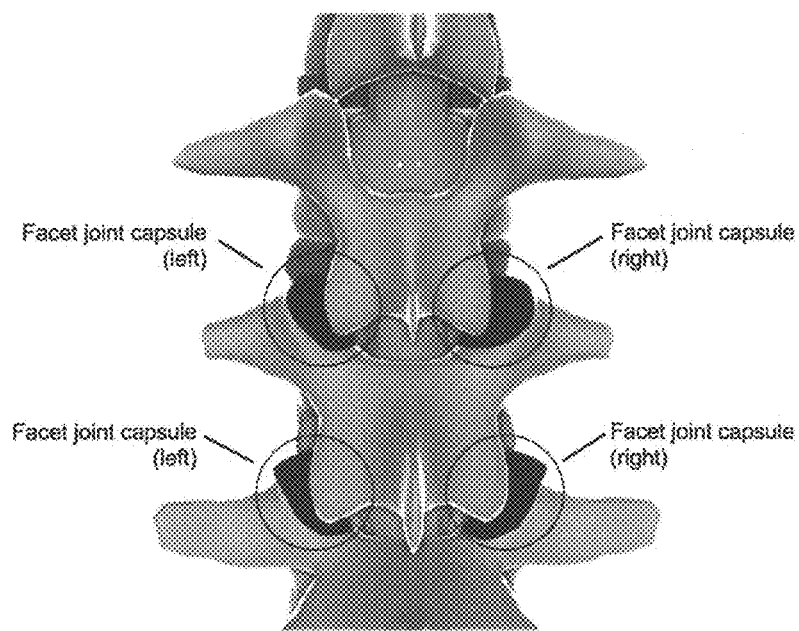

The 3D representation of the spine and/or sections of the spine may be generated using different methods. In accordance with one embodiment, the 3D representation may be formed through a sweeping and stitching function method such as that disclosed in the article entitled: B-Mesh: A Fast Modeling System for Base Meshes of 3D Articulated Shapes, http://citeseerx.ist.psu.edu/viewdoc/download?doi=10.1.1.357.7134&rep=rep1&type=pdf. This method results in creating surface geometry dynamically using software code to create surface geometry as seen in FIG. 5C. If any property is changed on a segment of the spinal cord the software code then generates new geometry for the spinal cord dynamically in real-time.

Non-uniform definition can be performed instead of sphere based as explained in the referenced paper. This allows non-uniform quad geometry to be created and adjusted.

Referring to FIGS. 6A-6E, within the spine may be facet joints. The facet joints may be defined as the joints in the spine that make your back flexible and enable you to bend and twist. The facet joints of the spinal are mainly defined as properties as such:
  1. Bone surface for each vertebra.
  2. Cartilage connected to the bone surface defined.
  3. Capsule surrounding the entire joint. Healthy facet joints have cartilage, which allows the vertebrae to move smoothly against each other without grinding.

For example the thickness of the cartilage can be set as an additional property. If the cartilage thickness is minor or non-existent then software code can process that property to render a more severe injury visually. Additionally if Cartilage is non-existent then software code can detect a more severe injury and create an additional injury such as an arthropathy process, which will create and/or modify geometry to show an impingement. The facet surface of the vertebra is predefined for each vertebra using a selected set of vertices and treated as a vertex group. This surface varies depending on the location of the vertebra (i.e. Cervical, Thoracic, or Lumbar). (See FIGS. 6A-D). Facet joints also include a capsule surrounding the joint. This capsule is defined as geometry and is created dynamically using software code and properties defined in other objects and data structures. (See FIG. 6E)

However, minor adjustment to the geometry of the facet joints may be made so as to refine the shape of the facet joint and/or other convex geometries.

As disclosed above, vertex groups may be used to tag the vertices belonging to parts of the vertebra. However, the vertex groups may only be defined for one half and a sorting function may be required to sort the connected joints, because an export process will define both sides under a single group. After each side is grouped by connected geometry, a convex hull or other defined method may be used to create the surface geometries. Volumetric methods such as metaball and isosurfaces can also be used to create surface geometry, which can be generated dynamically using software code.

Once the model of the anatomical structure has been formed, the user may perform manual adjustments to show/highlight certain injuries. For example, for the above embodiment where a spine is formed, the user may perform manual adjustments to the spine model to highlight:

Foraminal narrowing/foraminal stenosis
Spondylosis—Show as boney defect
Disk protrusion—Impingement on spinal cord
Herniated Disc—more serious usually has rupture of nucleus material/slipped disc
Facet joint arthropathy—Bone Spurs
Stenosis—Impingement of spinal cord
Central canal narrowing
Disk height Degeneration
Bone spurs end plates (VEP)
Subluxation—dislocations
Osteophytes While the above describes how a model of a spine may be formed and adjusted to show different injuries, the system and method may be used for other anatomical structures and should not be seen in a limiting manner. The above system and method may be used to create and analyze shoulder injuries, elbow injuries, knee injuries and/or other anatomical structures.

In operation, the system and method operate accordingly. The medical image data may be loaded into the system. A menu may be proved to allow a user to select an anatomical structure associated with the medical image data. Based on the medical image data, the system may select an existing database that may be closes to the medical image data loaded using a hybrid of statistical methods and/or text recognition based on additional medical records attached to the dataset. The user may then make adjustments to the selected model to more closely resemble the medical image data. The system may have interactive tools to aid the user in making adjustments to the selected model. Alternatively, or in addition to, the system may have artificial intelligence and/or machine learning algorithms that may assist with the classification and adjustment process in a much more efficient and expedient way. Thus, different injuries may be added either manually through the user interface and/or generated by the system through artificial intelligence and/or machine learning algorithms.

Figure 8A:
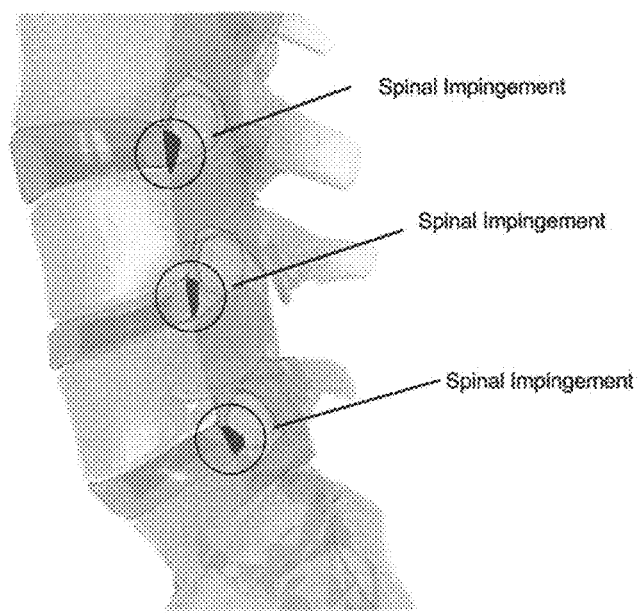
FIGS. 8A-B are illustrations showing impingements according to one embodiment of the present invention.
Figure 8B:
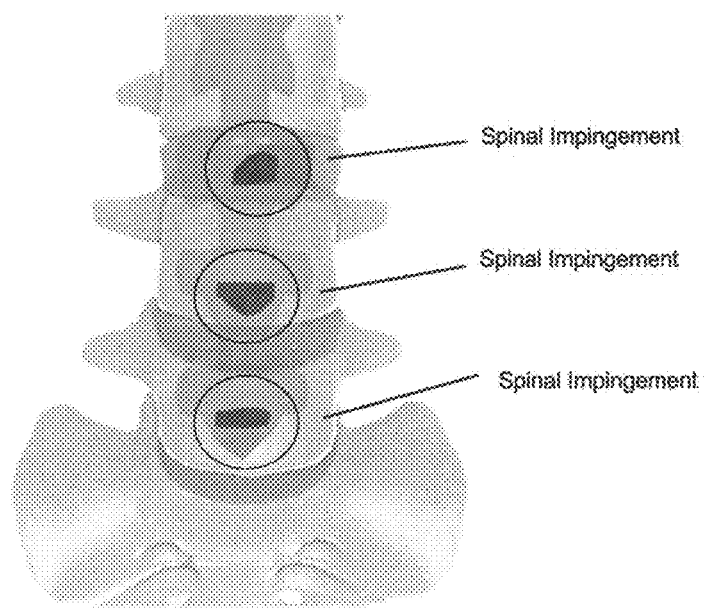

Based on the modified model, detection and visualization of the injured area may be performed. For example, semi auto detection may be used using algorithmic collision detection to identified potential injured areas. Collision detection typically refers to the computational problem of detecting the intersection of two or more objects. Thus, in the above example, impingements of the spine can be classified by collision detection as two vertebras may be identified as intersection together when a space should be seen (See FIGS. 8A-B). Further, disc height degeneration can be identified based on a distance between the vertebra endplate points. Additionally, the disc height or distance between vertebra endplates can be computed using a statistical method defined in a machine learned classifier or deep learning classifier performed on a series of datasets.

Auto detection may be used as well to identify potential injuries. The system may contain a database of classifiers. Based on the medical image data and the relationship to certain classifiers, the system may identify potential injuries. Additionally, a hybrid method using machine learning/statistical algorithms implementing functional composition of a variety of different algorithms such as machine-learning, deep learning, regression, image-based algorithms, feature detection algorithms, and such of the art. Moreover, spacial constraints will assist the hybrid method described above because of the novel ability to use a pre-defined dataset. For example facet injuries are going to be located spatially around the facet joints and the facet joints are dynamically created using defined points on geometry. This allows the machine based algorithm to create a bounding-box around the affected area in the 3D space/3D volumetric space. This helps eliminate the possible errors or false positives and provides significant performance improvement.

The system may generate a 3D model based on the property dataset defined. The 3D model may be displayed. The 3D model may have a key-frame sequence and/or animation sequence which represents the injuries in the dataset along with a slice cut sequence showing the classified areas. (aka segmentation) from different views/angles.

The foregoing description is illustrative of particular embodiments of the invention, but is not meant to be a limitation upon the practice thereof. The following claims, including all equivalents thereof, are intended to define the scope of the invention.

What is claimed is:

1. A computing device comprising:
a processor;
a display coupled to the processor;
a user interface coupled to the processor for entering data into the computing device; and
a memory coupled to the processor, the memory storing program instructions that when executed by the processor, causes the processor to:
load medical image data, wherein the medical image date is a plurality of two-dimensional images;
match the medical image data to an anatomical model stored in a database having a data set closest to the medical image data;

adjust at least one property on the anatomical model to form a modified three-dimensional anatomical model to match the medical data image; and detect if areas on the modified three-dimensional anatomical model exceeds predefined ranges indicating potential injured areas.

2. The computing device of claim 1, wherein the memory storing program instructions executed by the processor, causes the processor to store the modified three-dimensional anatomical model in the database as a new anatomical model.

3. The computing device of claim 1, wherein the medical imam date is a plurality of MRI scans.

4. The computing device of claim 1, wherein the memory storing program instructions executed by the processor, causes the processor to form the modified three-dimensional anatomical model using one of polygon modeling, non-uniform rational basis spline (NURBS) modeling, subdivision modeling, equation-based modeling and combinations thereof.

5. The computing device of claim 1, wherein the memory storing program instructions executed by the processor, causes the processor to form the modified three-dimensional anatomical model of a plurality of components, each component having manually adjustable properties to conform the modified three-dimensional anatomical model to the medical data image.

6. The computing device of claim 5, wherein the adjustable properties for at least one of the components comprises: height, radius, thickness, length, position, and scale.

7. The computing device of claim 5, wherein the memory storing program instructions executed by the processor, causes the processor to add data structures to at least one of the components, the data structure representing an abnormality to the at least one component.

8. The computing device of claim 5, causes the processor to add data structures to at least one of the components, the data structure being adjustable and represents an abnormality to the at least one component.

9. The computing device of claim 1, wherein the memory storing program instructions executed by the processor, causes the processor to:

divide each component into a plurality of sections, wherein each section having adjustable properties; and adjusting a desired section of a desired component to form the modified three-dimensional anatomical model matching the medical data image.

10. The computing device of claim 1, wherein the memory storing program instructions executed by the processor, causes the processor to add sub-structures to the anatomical model.

11. The computing device of claim 1, wherein the memory storing program instructions executed by the processor, causes the processor to:

define a specified region based on the medical image data; and match the specified region to a corresponding anatomical model.

12. The computing device of claim 1, wherein the memory storing program instructions executed by the processor, causes the processor to use Convolution based Neural Network (CNN) to match the medical image data to an anatomical model.

13. The computing device of claim 1, wherein the memory storing program instructions executed by the processor, causes the processor to form one of an automated video or animation creation of the modified three-dimensional anatomical model.

14. A computing device comprising:

a processor;

a display coupled to the processor;

a user interface coupled to the processor for entering data into the computing device; and a memory coupled to the processor, the memory storing program instructions that when executed by the processor, causes the processor to:

load medical image data, wherein the medical image data is a two-dimensional MRI scan;

match the medical image data to an anatomical model stored in a database having a data set closest to the medical image data, the anatomical model being a three-dimensional anatomical model;

adjust at least one property on the three-dimensional anatomical model to form a modified three-dimensional anatomical model to match the medical data image;

detect if areas on the modified three-dimensional anatomical model exceeds predefined ranges indicating potential injured areas;

store the modified three-dimensional anatomical model in the database as a new three-dimensional anatomical model; and form one of an automated video or animation creation of the modified three-dimensional anatomical model.

15. The computing device of claim 14, wherein the memory storing program instructions executed by the processor, causes the processor to form the modified three-dimensional anatomical model using one of polygon modeling, non-uniform rational basis spline (NURBS) modeling; subdivision modeling, equation-based modeling and combinations thereof.

16. The computing device of claim 14, wherein the memory storing program instructions executed by the processor, causes the processor to form the modified three-dimensional anatomical model of a plurality of components, each component having manually adjustable properties to conform the modified three-dimensional anatomical model to the medical data image to the two-dimensional MRI scan.

17. The computing device of claim 16, wherein the memory storing program instructions executed by the processor, causes the processor to:

divide each component into a plurality of sections, wherein each section having adjustable properties; and adjusting a desired section of a desired component to conform the modified three-dimensional anatomical model to the medical data image.

18. The computing device of claim 16, wherein the memory storing program instructions executed by the processor, causes the processor to add data structures to at least one of the components, the data structure representing an abnormality to the at least one component, the data structure having adjustable properties.

19. The computing device of claim 14, wherein the memory storing program instructions executed by the processor, causes the processor to;

define a specified region based on the medical image data; and match the specified region to corresponding anatomical model.

20. The computing device of claim 14, wherein the memory storing program instructions executed by the processor, causes the processor to use Convolution based Neural Network (CNN) to match the medical image data to an anatomical model.

\* \* \* \* \*